United States Patent
Kim

Patent Number: 6,166,357
Date of Patent: Dec. 26, 2000

[54] ELECTRIC MAT CONTAINING NEPHRITE JADE

[75] Inventor: Jun-Han Kim, #102-902 Hanjoo Apartment, Twaegye-dong 944, Choochun-shi, Kangwondo, Rep. of Korea

[73] Assignee: Jun-Han Kim, Kangwondo, Rep. of Korea

[21] Appl. No.: 08/961,024

[22] Filed: Oct. 30, 1997

[51] Int. Cl.[7] .................................................. H05B 3/34
[52] U.S. Cl. ................................................. 219/529
[58] Field of Search .................... 219/529, 212, 219/528, 354, 553, 211; 392/343, 346, 435, 439; 250/455.1, 493.1

[56] References Cited

U.S. PATENT DOCUMENTS

| | | | |
|---|---|---|---|
| 4,910,391 | 3/1990 | Rowe | 219/549 |
| 4,990,747 | 2/1991 | Konda | 392/435 |
| 5,218,185 | 6/1993 | Gross | 219/528 |
| 5,879,979 | 3/1999 | Kim | 428/328 |
| 5,935,483 | 8/1999 | Kong | 252/1 |

FOREIGN PATENT DOCUMENTS

| | | |
|---|---|---|
| 97-11094 | 9/1993 | Rep. of Korea . |
| 97-11095 | 9/1993 | Rep. of Korea . |

*Primary Examiner*—Philip H. Leung
*Assistant Examiner*—Daniel Robinson
*Attorney, Agent, or Firm*—Dickinson Wright PLLC

[57] ABSTRACT

The present invention provides an electric mat containing nephrite jade powder, which take advantage of effects of nephrite jade and completely shield the vibration of water vein and electronic wave.

The electric mat containing nephrite jade powder according to the present invention has multiply divided water-proof pockets (2) divided by conjunction lines (1), of which each space holds nephrite jade powder (4) of 150–300 mesh covered by a first nonwoven fabric (3), under which copper woven fabric (5), aluminum sheet (6) and a second nonwoven fabric (7) are inserted to face-contact the heater (8), under which jade cotton (9) is laid. By virtue of the structure described above, heat generated from the heater (8) is transmitted through the aluminum sheet (6) and the copper woven (5) to nephrite jade powder, from which far infrared is emitted.

8 Claims, 1 Drawing Sheet

ELECTRIC MAT CONTAINING NEPHRITE JADE

FIELD OF THE INVENTION

The present invention relates to an electric mat in which fine powder of nephrite jade has been indwelled.

More specifically, the present invention relates to an electric mat containing nephrite jade which is intended to show excellent effect of nephrite jade, for example promoting health condition by virtue of emission of far infrared of high wavelength as compared to the black body.

PRIOR ARTS

As is generally known, jade is largely divided into jadeite and nephrite jade.

Jadeite belongs to pyroxene family and has monoclinic system comprising silicic acid, aluminum oxide and soda. It is an intimate mass, and the hardness is comparable to that of crystal. It is transparent or translucent of black, blue green or green color. People usually call jadeite "jade".

Nephrite jade is an inorganic material having monoclinic system of inosilicates. The quality of nephrite jade is determined by the fine structure, and the finer the fiber, the better is the quality (Journal of Mining Promotion, 1993, new year issue, the Korea Mining Promotion Corporation).

According to a German medical literature [Mauda Palmer Die Verborgene, "KRAFF der KRISTALLE und der EDELSTEINE"], the two different ores, jadeite and nephrite jade, both comprise silicon and oxygen, as most of other jewels. However, Jadeite is formed of granular crystals while nephrite jade consists of lots of crystals and aggregates of microparticles having fibrous, hair-like structure. In particular, nephrite jade comprises three elements, Ca, Fe and Mg, which are good for human body, while jadeite comprises sodium and aluminum components. Thus, it has been recently reported that nephrite jade, when attached to the body, provides a considerable effect to the treatment of hypertension, diabetes, circulating system disorder, heart disease and kidney disorder.

Various products have been suggested in the field of mats or cushioned mattresses used as a utensil house good, but most of them intend to improve comfortable feeling by the use of cotton pads or the like.

Recently, mats or cushioned mattresses for promoting health condition are partly put to practical use. Representative examples include those which take advantage mineral components and far infrared emission of elvan, yellow soil or ceramic material.

In general, every mat or cushioned mattress for promoting health condition must essentially have the effect of far infrared emission, but the effect cannot reach the expected level, up to the present.

The present inventors have paid attention to the excellent far infrared emitting effect of nephrite jade and intensively studied for developing an electric mat using nephrite jade, and found that nephrite jade has much more far infrared emitting effect than elvan, yellow soil or ceramic material.

In addition, nephrite jade has been known to show the effects of promoting the circulation of blood, promoting sweating, alleviating pain, suppression and sound sleep when it is kept on one's body.

The effects of nephrite jade used in the present invention, which have been disclosed by the present inventors [Korea Patent Publication No. 97-11094 entitled "Synthetic resin containing nephrite jade powder and process for manufacturing the same"; Korea Patent Publication No. 97-11095 entitled "Synthetic resin fine particles for stuff of bedding containing nephrite jade powder"; Korea Patent No. 112822 entitled "Glass products containing nephrite jade powder and process for manufacturing the same"; Korea Patent No. 117906 entitled "A method of adding nephrite jade powder during the molding process of ceramic wares"; Korea Patent No. 118114 entitled "A method of adding nephrite jade powder during the process for producing soft drinks and the products made thereby"] include excellent effects of treating pathological symptoms (headache, numb feeling, indigestion, insomnia, or the like), removing impurities (such as heavy metals), improving the quality of water, promoting the growth of plants and animals, so that it can be widely applied to human life.

The characteristic of the nephrite jade according to the present invention is to emit far infrared ray having 9.1 micron wavelength, while the organic substances constituting human body generally are heat-absorbent and have heat-absorbing property with respect to a certain wave length. Every organic substance has its inherent vibrational frequency, and if the frequency conforms to the frequency of far infrared, exothermic phenomenon occurs from inside due to the resonance of the molecules. Thus when far infrared ray is to, be used in heating, it is most effective that far infrared ray which having a wavelength which can be easily absorbed by the material is emitted. Based on the findings, the present inventors completed the invention.

SUMMARY OF THE INVENTION

The object of the present invention is to provide an electric mat containing fine powder of nephrite jade so that the effect of promoting health condition can be much more enhanced.

Another object of the present invention is to provide a cushioned mattress having a constitution which can significantly hinder the electronic effects generated by a heater so that its harmfulness is fundamentally removed and the mattress promotes healthy conditions even if heating means by electric heating is applied to the mattress.

In order to achieve the objects mentioned above, the electric mat according to the present invention has a multi-ply divided water-proof pocket, of which each space holds far infrared emitting body comprising nephrite jade powder of 150–300 mesh covered by nonwoven fabric, under which copper woven fabric and aluminum sheet are laid, and nonwoven fabric is inserted beneath the aluminum sheet to contact the heater, under which jade cotton is inserted to form multi-layer structure.

<Description of the symbols of the main parts of the drawings>

| | |
|---|---|
| 1: conjunction line | 2: water-proof pocket |
| 3, 7: 1st and 2nd nonwoven fabric | 5: copper woven fabric |
| 4: nephrite jade powder | 8: heater |
| 6: aluminum sheet | 10: cover sheet |
| 9: jade cotton | |

DETAILED DESCRIPTION OF THE INVENTION

As a material for the water-proof pocket, urethane sheet that resists heat damage up to 230° C. is suitably used. It is desirable that some air is introduced inside of the pocket to give cushioning property.

The copper woven was made by plain weaving with using copper lines as latitudes or longitudes, and conventional fibrous yarn as longitudes or latitudes.

Jade cotton was prepared by adding an aqueous solution of nephrite jade powder during the cotton carding and drying thereof. The object of using jade cotton is for thermal insulation to prevent leakage of heat, and keep warm, increase emission of far infrared due to the emission of far infrared from nephrite jade powder. The thickness of jade cotton is preferably about 1.5 cm.

According to the present invention, the heat generated from the heater is transmitted through the aluminum sheet and copper woven to nephrite jade powder to cause emission of far infrared ray, so that the effect of nephrite jade can be effectively revealed.

During the process, the electronic effects generated by the heater are absorbed by aluminum sheet and copper woven, so that only a minimal effect reaches the user on the mat.

In particular, the far infrared absorbed into the body promotes metabolism, circulation of blood and production of enzymes, and activates aged cells to promote discharge of waste matter and surplus lipid, and inhibits the production of free fatty acids, fatty acid ester, cholesterol, surplus salt or uric acid, which may cause fatigue or aging, thereby giving the body health and youth.

Description of the Preferred Embodiment

The constitution of the present invention is now described in detail with reference to the drawings attached.

Figure 1:
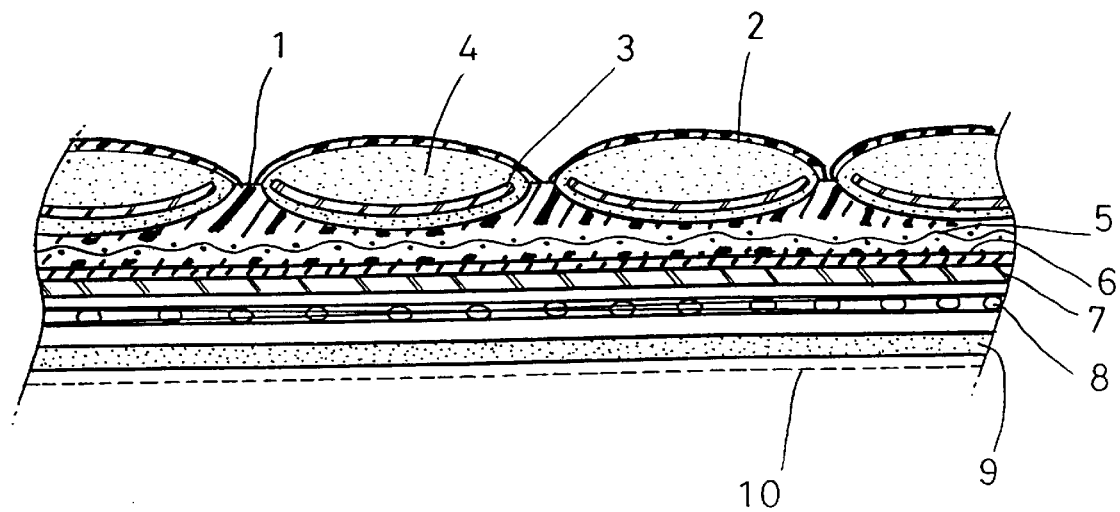
FIG. 1 is a partial cross-sectional view showing the constitution of main parts of the electric mat according to the present invention.

FIG. 1 is a partial cross-sectional view showing the constitution of main parts of the electric mat according to the present invention. In the upper layer, water-proof pockets (2) which are made of urethane sheet and multiply divided inside by conjunction lines (1) are laid. The water-proof pockets (2) are made of thermal resistant urethane sheet which endures temperature up to 230° C. Inside the pocket, the first non-woven fabric (3) of proper size together with nephrite jade powder (4) are accommodated so that nephrite jade powder (3) may not be get together in one side for the sake of the first nonwoven fabric (3) and be laid evenly.

Under the water-proof pockets (2), copper woven (5) is laid, under which aluminum sheet (6) is inserted.

The copper woven (5) was made by plain weaving with using copper lines having a diameter of 0.2–0.4 mm as latitudes or longitudes, and conventional fibrous yarn as longitudes or latitudes. This is provided in order to flow out electronic wave by earth connection through the electric means.

Under the aluminum sheet (6), the second nonwoven fabric (7), and then heater (8) are laid. Under the heater (8) jade cotton (9) is provided.

The second nonwoven fabric (7) has a substantial cushion between the heat line or heating pipe of the heater (8) and aluminum sheet (6) thereon, to isolate the two parts, in order not to cause an electric short owing to the contact of the two parts.

Jade cotton (9) beneath the heater (8) is prepared by a unique process contrived by the present inventors (Korean Patent Application No. 96-5866). When carding conventional cotton, aqueous nephrite jade solution is added and then dried to homogeneously distribute nephrite jade powder inside the cotton in a certain amount.

The overall appearance of the electric mat according to the present invention which has the constitution described above is shown in FIG. 2.

Figure 2:
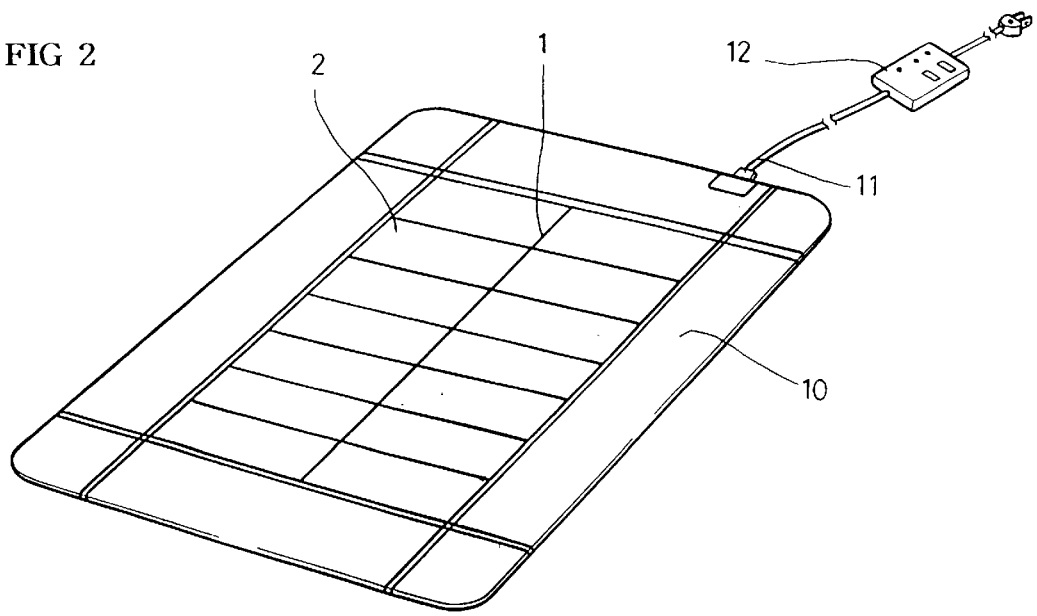
FIG. 2 is a perspective view showing the overall appearance of the electric mat according to the present invention.

In FIG. 2, the jade cotton (9), which is located at the lowest part, is packed with the cover sheet (10), so that only water-proof pockets (2) are exposed outside on the upper surface. The heater (8) inside the mat is controled by the user by means of a controller (12) which is electrically connected by a connector (11). Of course, the copper woven (5) also is connected by earth connection through the connector (11).

According to the present invention, the heat generated from the heater (8) is transmitted to nephrite jade powder (4) via the aluminum sheet (6) and copper woven (5) to have the powder emit far infrared. As the far infrared is emitted by nephrite jade powder as a medium, the effect is more excellent than that of other kind of far infrared emitting substances.

The far infrared experimental study of nephrite jade powder used in the present invention was performed.

TABLE 1

| Sample | Jade Powder |
|---|---|
| Appearance | White powder |
| Experimental method | KS L 100 - 94 |
| Turning strength (N/cm) | 3.64 |
| Emission ratio (5–20 $\mu$m) | 0.91 |
| Emitted energy (W/m', $\mu$m, 40° C.) | $3.66 \times 10^2$ | note) The results by using FT-IR Spectrometer, as compared to the measurement of Black Body (by Korea Experimental Research Center for Building Materials).

According to the present invention, leakage of heat through the lower part of the heater (8) is prevented by jade cotton (9). Jade cotton prevents the leakage of heat from the heater (8) and increase the thermal efficiency. Further, the heat from the heater (8) warms nephrite jade powder to generate far infrared ray, which redoubles far infrared ray emitted from the water-proof pockets (2) of the upper part.

As jade cotton (9) basically forms cushioning of the mat, proper thickness is required, preferably 1.5 cm or more.

The results of clinical test using the bedding (electric mat) prepared according to the present invention showed 88% of remedial value, that is similar to the results using the nonwoven fabric containing nephrite jade powder as a medical mattress [Korean Patent Application No. 96-5866].

Method and Standard for Selection of Patients to Be Tested

Among the patients who were under the treatment in Korea Medicine Hospital attached to Daejeon University, 25 people having symptoms of headache, insomnia, uneasiness and numbed feeling of hands or feet were selected as the object of the clinical test.

Method and Items of Observation

Patients under treatment in the hospital having headache, insomnia, dizziness, uneasiness of numbed feeling were made to use the product of the present invention for a certain period (10 days or more), and the condition and change of body were observed.

Method and Standard for Evaluation

A. Standard for evaluation: based on the condition of the first medical

B. Method for evaluation: as shown below

|   | Condition | Evaluation (5) |
|---|---|---|
| 1 | No effect or insignificant effect | <70 |
| 2 | Positive effect | ≧70 |
| 3 | Substantial effect | ≧80 |
| 4 | Perfect cure or so | ≧90 |

Results of Clinical Test (Main Effects)

1. Headache was alleviated.
2. Insomnia or uneasiness was recovered.
3. Numbed feeling of hands and feet was alleviated.
4. Symptoms such as indigestion were alleviated (according to the clinical test).

Results from Method of Evaluation

| Symptoms | No effect or so <70% | Positive effect ≧70% | Substantial effect ≧80% | Perfect cure or so ≧90% | Total |
|---|---|---|---|---|---|
| Headache | 2 | 3 | 5 | 1 | 11 |
| Insomnia | 0 | 2 | 4 | 1 | 4 |
| Uneasiness | 1 | 1 | 1 | 2 | 5 |
| Numbed | 0 | 1 | 1 | 1 | 3 |
| feeling | | | | | |
| Indigestion | 0 | 0 | 2 | 0 | 2 |
| Total | 3 (12%) | 7 (28%) | 10 (40%) | 5 (20%) | 25 (100%) |

As described above, the present invention provides the effects of nephrite jade such as promoting the circulation of blood, promoting sweating, alleviating pain, suppression and sound sleep, as well as those of far infrared ray to the user. Thus the effect of promoting health condition is substantially excellent. As the loss of heat is minimized in the structure of the electric mat according to the present invention, the power consumption and the cost for using were decreased. In addition, the electric mat according to the invention can be used in security as an electric heating means.

What is claimed is:

1. An electric mat containing nephrite jade powder, comprising:

a plurality of water-proof pockets divided by conjunction lines, wherein each pocket holds nephrite jade powder 150–300 mesh, and a first nonwoven fabric of a predetermined size for distributing said powder within said pocket, under which a copper woven fabric, an aluminum sheet, and a second nonwoven fabric are inserted to face-contact a heater, wherein a jade cotton layer is disposed beneath said heater.

2. The electric mat according to claim 1, wherein said water-proof pockets are made of urethane sheets having a thermal resistance up to 230° C.

3. The electric mat according to claim 1, wherein said jade cotton layer helps to prevent the leakage of heat from said heater on the underside of said mat, and said jade cotton layer has homogeneously distributed nephrite jade powder therein.

4. The electric mat of claim 1, wherein said jade cotton layer comprises a layer of cotton with nephrite jade powder dispersed therein.

5. The electric mat of claim 1, wherein said jade cotton layer uses nephrite jade.

6. The electric mat of claim 1, wherein air is contained in each of said water-proof pockets to provide a cushioning effect for said mat.

7. The electric mat of claim 1, wherein said copper woven fabric, aluminum sheet, and second nonwoven fabric, are positioned between said plurality of pockets and said heater.

8. The electric mat of claim 7, wherein said second nonwoven fabric is positioned adjacent and above said heater.

* * * * *